United States Patent [19]

McCarthy

[11] Patent Number: 5,288,789
[45] Date of Patent: Feb. 22, 1994

[54] FOAM CONTROL IN FERMENTATION BROTHS WITH A CONDENSATE OF ALKYLPHENOL AND ALDEHYDE THAT HAS BEEN POLYOXYALKYLATED

[75] Inventor: Kevin J. McCarthy, University City, Mo.

[73] Assignee: Petrolite Corporation, St. Louis, Mo.

[21] Appl. No.: 858,202

[22] Filed: Mar. 26, 1992

[51] Int. Cl.$^5$ .................. C12N 1/00; C12N 1/34; C08F 283/06; C08G 65/02
[52] U.S. Cl. ..................... 435/243; 435/246; 525/404; 528/393
[58] Field of Search ............... 435/246, 243; 525/404; 528/393

[56] References Cited

U.S. PATENT DOCUMENTS 3,862,243  1/1975  Bellos ........................ 260/615 B
4,612,352  9/1986  Schäfer ........................ 525/404

OTHER PUBLICATIONS

BIO-1395 Brochure, ©Copyright 1988, Petrolite Corporation.

Primary Examiner—Douglas W. Robinson
Assistant Examiner—Deborah K. Ware
Attorney, Agent, or Firm—Kenneth Solomon

[57] ABSTRACT

A method is disclosed for controlling foam in a fermentation broth by adding to the fermentation broth an effective amount of a composition comprising a compound corresponding to the formula:

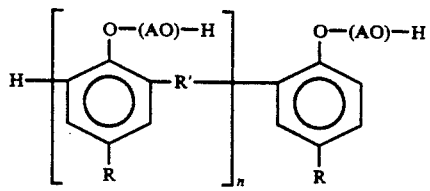

wherein AO is an oxyalkylene copolymer moiety of oxypropylene and oxyethylene units, each oxyalkylene copolymer moiety having a molecular weight of at least about 300 and an oxypropylene to oxyethylene molar ratio of from about 2:1 to about 10:1, n is an integer from about 1 to about 20, R is an alkyl group of from about three to about twelve carbon atoms, and R' is methylene or substituted methylene. The composition can be added to fermentation broths to prevent the formation of foam or to reduce foam which has already formed. The above defined composition is also disclosed in a form free of solvent, such as xylene.

19 Claims, No Drawings

FOAM CONTROL IN FERMENTATION BROTHS WITH A CONDENSATE OF ALKYLPHENOL AND ALDEHYDE THAT HAS BEEN POLYOXYALKYLATED

BACKGROUND OF THE INVENTION

This invention relates to a method for the prevention and reduction of foam in fermentation broths. More particularly, it relates to such a method wherein the foam is controlled by the addition of chemical agents. Foams occur as an undesirable incidental feature in many systems. Although some theories of foam formation have been proposed, little is known about why some compounds are antagonistic to foams while others are not. Of considerable frustration to those in the art of foam control is the fact that each foam control problem is unique, calling for a different compound for effective foam control. Some materials are useful only to prevent foam formation ("antifoams") while some are useful only to reduce foam which has already formed ("defoamers"). Efforts to predict which compound will work in a given system have not proven successful. As a result, foam control is basically an empirical art.

The following quotations summarize the views of experts in the field of foam control:

"More than 300,000 chemicals are now available, thousands of which work as defoamer ingredients in particular systems. It is difficult then to pinpoint exactly which defoamer will work where, and why, so it is best to leave the problem to specialists. Another reason is that all variables must be considered when formulating defoamers compatible with production systems."
*Foam Control, A Misunderstood Concept*, by Marshall Ott, Household & Personal Products Industry, February 1978.

"Because of the variety of materials to be defoamed and the extreme conditions of operation, no single material has universal application as a chemical antifoam. Some systems are predominantly aqueous, whereas others are organic mixtures with only a trace of moisture; in others the presence or absence of solids may be a factor. Operational conditions vary from high pressure steam generation to vacuum distillation; jet fuels may foam on the plane's ascent, and low-boiling substances may cause foaming in the oil-well pumping of certain gaseous petroleum crudes. To add to the difficulties, *the antifoam for one system may be a foamer in another*." (Emphasis added).
*Encyclopedia of Polymer Science and Technology*, Vol. 2, 1964, pg. 164 (Antifoaming Agents).

"Thus a paper mill may easily use six or more defoamers for routine coated paper manufacture. The same holds true for other defoamer applications. For example, a paint manufacturer may need different defoamers for the various phases of paint production such as in the pigment grind, letdown, can filling, and mill effluent. Manufacturers of textiles, sugar from sugar beets, and fertilizers require different defoamers for the various phases of production."
*Encyclopedia of Chemical Technology*, Vol. 7, 1979, pg. 433 (Defoamers).

"One of the fruits of success in this endeavor would be to diminish the empiricism that at present characterizes the search for an optimum foam inhibitor."
*Mechanisms of Foam Stabilization and Antifoaming Action*, by S. Ross, Rensselaer Polytechnic Institute, Chemical Engineering Progress. Vol. 63, #9, pg. 46.

"It is well known that the performance of an antifoam or foam preventer is strongly dependent on the type of foaming system involved. However, little is known about the specific parameters which influence antifoaming activity."
*Mechanism of Antifoaming Action*, by R. D. Kulkarni et al, J. of Colloid and Interface Science, Vol. 59, #3, May 1977.

"An important problem of commercial aerobic fermentation processes consists of the foaming of media, and the suppression of this tendency. In the fermentation of antibiotics it is particularly important to choose the correct method for the suppression of foaming, and to choose a suitable anti-foam agent."
*The Foams of Fermentation Broths*, by Laszlo Szarka, Biotechnology & Bioengineering, Vol. XI, pg. 701, 1969.

Foaming in fermentation broths is particularly problematic in that the material chosen must be compatible with sterilization procedures, non-toxic to the fermentation organism, non-interfering with extract of the desired fermentation product, as well as be an effective foam control agent. In particular, the pharmaceutical industry has a long-felt need for more effective foam control agents.

From a technical standpoint there are a large number of instances where silicone foam control agents are preferred because of their superior performance. However, since silicones are often 3 to 10 times more expensive than other foam control compounds, the non-silicones are economically preferred, even if their performance is inferior. Therefore, it would be desirable to provide a highly effective and economical foam control agent suitable for use in fermentation broths.

Suppression of foams in fermentation broths is known. Examples of typically used compounds include silicone emulsions, silica dispersions, pure silicone fluids, polypropylene glycol, and various block copolymers of propylene oxide and ethylene oxide.

U.S. Pat. No. 3,862,243 (Bellos - Petrolite) discloses compounds of the general formula

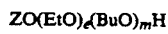

ZO(EtO)$_e$(BuO)$_m$H where Z is a hydrocarbon group, EtO is an ethoxy moiety, BuO is a butoxy moiety, e is from 3 to 30 and m is from 2 to 20. This patent teaches that these compounds "are useful in controlling foams in many different types of systems. They control foam encountered in gas-treating systems in which a mixture of glycols and alkanolamines is used to dehydrate and purify natural gas; in activated-sludge-process sewerage plants, particularly in aeration basins and elsewhere; in protein adhesives solutions, such as casein and soybean adhesives as used in the plywood industry; in latex adhesives, printing inks; aqueous emulsions paints; etc."

Similar to the teachings of the above patent, commercial products are available which have the general formula

wherein PrO is a propoxy moiety, p is from 5 to 50, and the other symbols are as defined above. These compounds are sold as antifoams for detergent systems such as dishwashing detergents, rinse aids, and metal spray cleaning detergent compounds; caustic scrubbers; fermentation broths and rolling oil formulations.

Numerous other polyalkoxylated compounds are also known and many of these compounds are known to be useful as foam control agents, albeit in systems far removed from fermentation broths. For example, a form of the composition found to be useful in the present invention for control of foam in fermentation broth has seen limited use as a defoamer in the adhesives industry. However, there has been no teaching or suggestion of its applicability to the radically different field of fermentation processes, especially with respect to the distinctive fermentation broths. Thousands of foam control agents exist, each of which is effective with respect to certain systems, and even those found to be effective in a particular system often are effective only as to certain conditions for that system. Thus, there has been no indication that such compositions, out of thousands of possibilities, would be satisfactory defoamers for fermentation broths.

SUMMARY OF THE INVENTION

The invention centers around the discovery that compounds of the formula

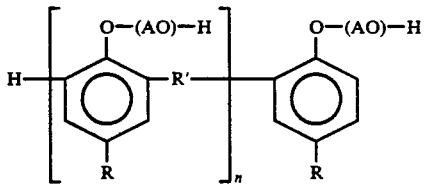

wherein AO is an oxyalkylene copolymer moiety of oxypropylene and oxyethylene units, each oxyalkylene copolymer moiety having a molecular weight at least about 300 and an oxypropylene to oxyethylene molar ratio of from about 2:1 to about 10:1, n is an integer from about 1 to about 20, R is an alkyl group of from about three to about twelve carbon atoms, and R' is methylene or substituted methylene, can be added to fermentation broths to prevent the formation of foam or to reduce foam which has already formed. The method of the invention is economical and surprisingly effective.

DETAILED DESCRIPTION OF THE INVENTION

In the specification and claims, numerical values are not critical unless otherwise stated. That is, the numerical values may be read as if they were prefaced with the word "about" or "substantially"

In accordance with the present invention, it has been discovered that foam in fermentation broth can be controlled by addition to the broth of a compound of the formula

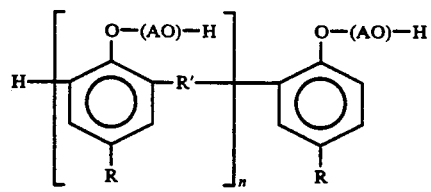

wherein AO is an oxyalkylene copolymer moiety of oxypropylene and oxyethylene units, each oxyalkylene copolymer moiety having a molecular weight at least about 300 and an oxypropylene to oxyethylene molar ratio of from about 2:1 to about 10:1, n is an integer from about 1 to about 20, R is an alkyl group of from about three to about twelve carbon atoms and R' is methylene or substituted methylene.

In particular, it has been discovered that such fermentation broth foam control can be achieved with an alkylphenol and aldehyde condensation reaction product that has been propoxylated and ethoxylated under dehydration conditions. Surprisingly, polyalkoxylated alkylphenol/aldehyde products have now been found to be an extremely effective foam control agents for fermentation broths, including yeast and antibiotic fermentation broths as well as agricultural fermentation broths. In fact, it is believed that the products would be effective foam control agents for essentially any type of fermentation broth. Moreover, the product has been found to be relatively nontoxic to fermentation organisms and to be non-interfering with extraction of the desired fermentation product.

The compositions useful as foam control agents in the methods of this invention may be prepared as follows. To a clean stainless steel continuously stirred tank reactor is added (at 50° C.) a solvent (preferably xylene), alkylphenol and an acid catalyst in an approximate weight ratio of 32:28:1. Of course, other proportions, especially other solvent to alkylphenol proportions, may be employed, depending on, for example, the desired concentration of alkylphenol resin in the mixture. Substantially lower alkylphenol concentration is less desirable as being wasteful. Any alkylphenol wherein the alkyl group has about three to about twelve carbon atoms may be used. Preferably, the alkyl group has about four to about nine carbon atoms. Although the alkyl group may be primary, secondary or tertiary, the availability of phenols with tertiary alkyl groups especially tertiary butyl-, octyl- and nonyl-phenols, particularly t-butylphenol, makes such phenols particularly desirable. Although the alkyl group may be at the ortho position, the para position is preferred. The catalyst may be dodecylbenzene sulfonic acid (DDBSA) or another acid catalyst.

The mixture is then heated to about 120 to about 125° C. and a lower aldehyde is added at that temperature in about an equal (or slightly excess) molar amount as the alkylphenol. While any lower aldehyde (aldehydes of less than about eight carbon atoms) such as furfural, acetaldehyde and formaldehyde, are understood to be appropriate, the cost and availability of formaldehyde makes it particularly suitable. For example, about 0.9 to about 1.2 (preferably about 1 to about 1.1) moles of aldehyde (such as formaldehyde in the form of formalin; i.e., 37% formaldehyde) per mole alkylphenol in the solvent/alkylphenol/catalyst mixture may be added over a period of several hours while water is azeotroped off continuously. The resulting mixture is maintained at a temperature up to about 135° C. and is stirred for an additional hour to complete the removal of water. The mixture is then neutralized and made basic by adding a base slowly. For example, a small amount of a 50% aqueous solution of sodium hydroxide may be added slowly so as to make up about 1.5% of the reaction mixture, which is then heated to about 135° C. for azeotropic distillation and held at that temperature until water is no longer being removed. The alkylphenol/aldehyde reaction products have been found to comprise alkylphenol formaldehyde resins of about two to about twenty or twenty-one alkylphenol groups, generally about seven to about fifteen groups.

The alkylphenol/aldehyde reaction product then may be polyoxyalkylated under dehydration conditions. Generally, the reaction product is polyoxypropylated and polyoxyethylated. The propylene oxide and ethylene oxide may be added and reacted in either order; i.e., propylene oxide followed by ethylene oxide or vice versa, to form a block copolymer moiety of the formula —(PrO)$_x$(EtO)$_y$— or —(EtO)$_y$(PrO)$_x$—, or the oxides may be premixed to form a random copolymer moiety in which the PrO and EtO units are distributed relatively randomly, or in multiple block copolymers. At least about five (preferably at least about ten) moles of propylene oxide and at least about one (preferably at least about two) moles of ethylene oxide per mole alkylphenol unit are believed to be sufficient for oxyalkylation of the alkylphenol units. Thus, the preferred minimum molecular weight of the oxyalkylene copolymer moiety is about 300. Preferably, the minimum is about 600. More preferably, however, greater polyoxyalkylation; e.g., at least about twenty moles propylene oxide, is desired, and the upper limit is provided only by the economics and other practical considerations as the benefits provided by each additional mole diminish. Practically, therefore, at most about 100 moles of propylene oxide and about thirty moles of ethylene oxides are added. Thus, about five to about 100 moles propylene oxide and about one to about thirty moles ethylene oxide, are added to the mixture per mole alkylphenol unit, the molar ratio of propylene oxide to ethylene oxide being from about 2:1 to about 10:1, preferably about 4:1 to about 6:1. Preferably, about ten and even more preferably about twenty) to about 100 moles propylene oxide and about two to about thirty moles ethylene oxide are added, resulting in a preferred minimum molecule weight for the oxyalkylene copolymer moiety of about 600 and an even more preferable minimum of 1,200.

However, it has been found that competing reactions result in significant production of side products of approximate average formulas CH$_2$=CHCH$_2$O(-PrO)$_a$(EtO)$_b$H and CH$_3$CH=CHO(PrO)$_a$(EtO)$_b$H and average molecular weight of up to about 3,000 (a:b being about 2:1 to about 10:1) if propylene oxide is added before ethylene oxide and CH$_2$=CH—CH$_2$—O(-PrO)$_a$H and CH$_3$—CH=CH—O(PrO)$_a$H and average molecular weight of 2,000 if ethylene oxide is added before propylene oxide. Other related side products are possible. Thus, particularly for greater molar additions of the propylene oxides, the actual numbers of oxypropylene and oxyethylene groups in each oxyalkylene copolymer moiety tend to be less than the numbers moles of propylene oxide and ethylene oxide added. For example, the addition of 74 moles of propylene oxide and 13 moles of ethylene oxide per mole alkylphenol have been found to result in a number of oxypropylene and oxyethylene groups in each oxyalkylene copolymer moiety on the order of about 30 and 5, respectively. The preferred range for the average number of oxypropylene group is therefore about five (more preferably about ten) to about forty, even more preferably about twenty to about forty. The preferred range for the average number of oxyethylene groups is about one (more preferably about two) to about thirty, even more preferably about two to about twenty, especially about two to about ten. The solvent (e.g., xylene) is then removed, such as by initiating a vacuum (22-24 inches) and a subsurface nitrogen purge at 135° C., increasing the temperature to 165° C. and maintaining that temperature for about two hours to complete the solvent removal. The final product, therefore, is free of xylene and comprises a polyoxyalkylated composition of the theoretical formula

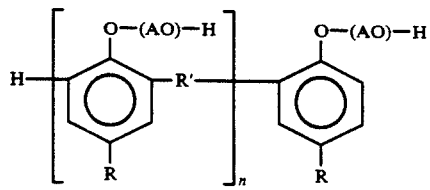

wherein AO is an oxyalkylene polymer moiety of oxypropylene and oxyethylene units, each oxyalkylene copolymer moiety having a molecular weight at least about 300, preferably at least about 600, and an oxypropylene to oxyethylene molar ratio of from about 2:1 to about 10:1, n is an integer from about 1 to about 20, R is an alkyl group of from about three to about twelve carbon atoms, R' is methylene or a substituted methylene. More preferably, the oxyalkylene polymer moiety has an average molecular weight of at least about 1,200, such as about 1,200 to about 5,000, most preferably about 1,200 to about 3,000. The preferred groups identified by R have been discussed above with respect to the alkyl group of the alkylphenol. R' is the residue from the aldehyde. Thus, methylene and substituted methylenes having less than eight carbon atoms are preferred, and for the preferred aldehyde, formaldehyde, R' is methylene. Preferably, R' is methylene or a substituted methylene of at most about three carbon atoms. It should also be noted that, as in the case of furfural, the substituted methylene may contain hetero atoms.

Thus, for example, the t-butylphenol/formaldehyde reaction product may be reacted under dehydration conditions, first with propylene oxide, and then with ethylene oxide, in approximate molar ratios of 74:1 and 13:1, respectively, based on t-butylphenol. This particular product has been employed on a limited basis in the adhesive industry. For the new application to fermentation broths, it has been found desirable to increase the flashpoint of the product by distilling off the solvent (xylene).

In the case of the addition of propylene oxide and then ethylene oxide, t-butylphenol and formaldehyde, the oxyalkylated alkylphenol/aldehyde reaction product believed to be of the formula:

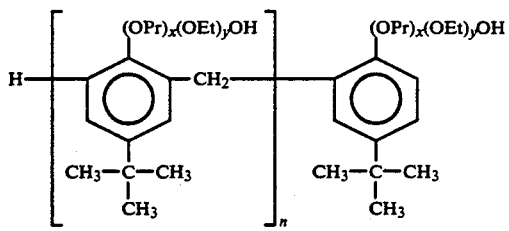

wherein Pr represents 1,2-propylene, Et represents ethylene, n is an integer from about 1 to about 20, x is an integer from about 5 (preferably from about 10, more preferably from about 20) to about 40 and y is an integer from about 1 (preferably from about 2) to about 3 (preferably to about 20, especially to about ten). It is believed that the reaction product comprises a distribution of such compositions over the range of n, x and y, and that, generally, n preferably averages about 1 to about 14, more preferably about 6 to about 14, typically about 6 to about 8. Theoretically, in the case in which 74 moles of propylene oxide and 13 moles of ethylene oxide are added per mole of t-butylphenol, assuming complete conversion, x would average about 74 and y about 13. However, because of the side reactions, it is believed that the actual average values of x and y are about 30 and 5, respectively.

The compounds are used in a fermentation broth. By "fermentation broth" is meant an aqueous dispersion of individual cells and nutrients for those cells, from which a metabolic product or cell culture is ultimately extracted; or an aqueous dispersion of the nutrients alone, prior to addition of the cells. Although the cells can be from multicellular organisms (particularly those from "immortal" cell lines or those used to support virus cultures), the cells are preferably bacteria or fungi. The desired metabolic product or cell culture extracted from the broth can be a cell culture but is preferably a metabolic product, more preferably a pharmaceutical. By "pharmaceutical" is meant a substance (other than a food) intended to be administered to a mammal to diagnose, cure, prevent, or treat a disease, by chemical action. Exemplary pharmaceuticals include antibiotics, hormones, steroids, and agents intended to alter immune response. Preferred pharmaceuticals are antibiotics.

In addition to water and optionally the cell line, the fermentation broth will contain nutrients for the cells. In general, the nutrients will comprise a source of carbon, nitrogen, trace elements (minerals), and organism-specific requirements. Carbon sources include monosaccharides, disaccharides, polysaccharides, alcohols, carboxylic acids, fats, and hydrocarbons. Nitrogen sources often also include carbon, and are represented by ammonia, urea, bean meal, grain meal, seed meal, fish meal, cornsteep liquor, and yeast extracts. Trace elements can be specifically added (usually in the form of salts) but may be supplied by using well water or municipal tap water. Some organisms also require one or more specific additional compounds which they are not able to synthesize. These typically include amino acids, purines, or pyrimidines. The nutrients in fermentation broths are well known to those skilled in the art.

The oxyalkylated compounds useful in the invention are added to fermentation broths to prevent foam formation ("antifoams") or to reduce foam which has already formed ("defoamers"). As an antifoam the compounds are simply blended with the broth and as a defoamer the compounds are simply dropped or sprayed onto the foam. The use of diluents is not necessary and in fact is not desirable because of the possibility of the diluent interfering with either the fermentation process or the activity of the defoamer/antifoam compounds.

As antifoams the polyoxyalkylated compounds are added in an effective amount. That is, an amount sufficient to retard the generation of foam in the broth. Although the precise amount will vary depending o the exact nature of the broth and the choice of polyoxyalkylated compound, generally the polyoxyalkylated compound will be used at 5 to 5,000, desirably 25 to 3,000, preferably 25 to 2,000, more preferably 50 to 1,000 and optimally 200 to 1,000 ppm (parts per million) (weight basis).

As defoamers the polyoxyalkylated compounds are added in an effective amount. That is, an amount sufficient to reduce the volume of foam present on the broth. Since the precise amount will vary depending not only on the exact nature of the broth and the choice of polyoxyalkylated compound, but also on the existing foam volume and the presence of any antifoam compounds, it is difficult to state in narrow terms the amount of polyoxyalkylated compound to use. However, in general, the polyoxyalkylated compound will be used at 5 to 5,000, desirably 25 to 3,000, preferably 25 to 2,000, more preferably 50 to 1,000 and optimally 200 to 1,000 ppm (parts per million)(weight basis).

The invention will be further illustrated in the following examples. In the examples, all parts and percentages are by weight unless otherwise specified.

EXAMPLE 1

Xylene (4,063 lbs.), para t-butylphenol (3,530 lbs.) and dodecylbenezene sulfonic acid (1.26 lbs.) were added at 50° C. to a clean stainless steel continuously stirred tank reactor. The mixture was then heated to about 12020 to 125° C. and formalin (37% formaldehyde) (2,129 lbs.) was added at 120°-135° C. over a period of several hours, during which time, water was azeotroped off. The resulting mixture was stirred for an additional hour to complete water removal. A 50% aqueous solution of sodium hydroxide (152 lbs.) then was added slowly, after which the new mixture was heated to 135° C. and held at that temperature until water was no longer removed.

An amount (633 lbs.) of the resulting reaction product was then added to a clean stainless or carbon steel reactor under vacuum of 18 to 20 inches and an agitator started. Xylene (219 lbs.) was then added to the reactor and the vacuum broken with nitrogen. Dry sodium hydroxide (21 lbs. of 57.5% active) was then added. To initiate dehydration, a vacuum of 20 to 24 inches was pulled on the reactor and the reactor was heated to a temperature in the range of 113° to 118° C. with minimum vacuum of 14 inches and operated with reflux at that temperature until water was no longer removed (about half an hour). The reflux was then shut down and the vacuum broken with nitrogen. The vacuum was reinstated and the temperature set to about 115° C. Propylene oxide (8,066 lbs.) was then charged to the reactor at a rate low enough to maintain the temperature between 115° and 125° C. and the pressure below about 45 psig. After addition of the propylene oxide, the temperature was raised to 125° C. and held there until the pressure stabilized, about an hour, to ensure complete reaction of the propylene oxide. The same procedure was then repeated for addition of ethylene oxide (1,061 lbs.). A 22-24 inch vacuum and a subsurface nitrogen purge were initiated on the reaction mixture to remove xylene and the setpoint was increased to 165° C. and held there for two hours to complete the xylene removal. Analysis of the resulting product suggested that the molar ratios of propylene oxide and ethylene oxide to alkylphenol in the alkylphenol product were about 30:1 and 5:1, respectively. The average number of alkylphenol groups in the product was found to average about 7. Side products present in about an equal weight ratio as the alkylphenol were of the approximate formula

$CH_2=CHCH_2O(PrO)_{29}(EtO)_5H$ and
$CH_3CH=CHO(PrO)_{29}(EtO)_5H$.

EXAMPLE 2

Antifoams were tested on two proprietary fermentation broths differing only in their nitrogen source. One of the broths was described as a contemporary broth and the other as a more economical broth. These broths were agricultural fermentation media and were supplied by a third party. A commercial silicone antifoam, which is a high viscosity polydimethylsiloxane fluid (referred to herein as HVPDS), had been found to inhibit the foam at 400 ppm, but was extremely toxic to the microorganisms at that level. A standard air sparge antifoam test was conducted with the fermentation media heated to 30° C. The pH of the media was measured at 6.4. Air flow was about 4.0 SCFH. Media samples (100 ml each) were evaluated in a 500 ml graduated cylinder. Doses of antifoam were added to samples of the media. Periodic foam height measurements were taken as recorded against the ml markings on the graduated cylinder and the results are shown in the following tables, with the antifoam of Example 1, above, identified as "Ex. 1". An antifoam of the general description $ZO(EtO)_e(PrO)_pH$ (Z is a hydrocarbon, e is 3–30, p is 5–50) was also tested for comparison and is identified in the tables as antifoam X.

| Anti-foam | Dose (ppm) | Foam Height (mls) at | | | | | |
|---|---|---|---|---|---|---|---|
| | | 0.5 min. | 1 min. | 2 min. | 3 min. | 4 min. | 5 min. |
| BROTH 1 | | | | | | | |
| None | — | >400 | | | | | |
| HVPDS | 200 | 135 | 190 | >400 | | | |
| " | 500 | 85 | 150 | 235 | 360 | 375 | >400 |
| " | 1,000 | 105 | 185 | 210 | 225 | 295 | 315 |
| X | 100 | 45 | 50 | 85 | 165 | 190 | >400 |
| " | 200 | 40 | 30 | 40 | 60 | 85 | 160 |
| " | 500 | 15 | 15 | 15 | 15 | 15 | 15 |
| " | 1,000 | 25 | 25 | 20 | 20 | 20 | 20 |
| Ex. 1 | 200 | 10 | 15 | 15 | 40 | 60 | 65 |
| " | 500 | 5 | 5 | 5 | 5 | 5 | 5 |
| " | 1,000 | 10 | 10 | 10 | 10 | 10 | 10 |
| "* | 500 | 15 | 15 | 25 | 65 | 70 | 75 |
| BROTH 2 | | | | | | | |
| None | — | >400 | | | | | |
| HVPDS | 100 | 55 | 45 | 40 | 40 | 65 | 65 |
| " | 200 | 55 | 35 | 25 | 25 | 25 | 35 |
| X | 200 | 85 | 40 | 45 | 65 | 90 | 135 |
| " | 500 | 25 | 15 | 10 | 10 | 10 | 10 |
| " | 1,000 | 30 | 10 | 10 | 10 | 10 | 10 |
| Ex. 1 | 200 | 40 | 35 | 35 | 45 | 55 | 40 |
| " | 500 | 20 | 20 | 20 | 20 | 20 | 20 |
| " | 1,000 | 5 | 5 | 10 | 10 | 10 | 15 |

*This dose was added as a defoamer on an already developed 400 ml foam, which crashed within 5 seconds after addition of the dose and then redeveloped as shown.

For each broth, the untreated media produced greater than 400 ml of foam in six seconds.

EXAMPLE 3

Various antifoams were tested on four variations of an antibiotic fermentation broth containing 60% solids and 15% lard oil, the variations differing in treatments and fermentation exposure. Samples of broths were tested according to the procedures described in Example 2, above, but with the air flow about 4.5 SCFH. The pH of the samples was 5.2 to 5.4. The antifoam was added neat via a microliter syringe, but was injected into the surface foam formation after the induced air had generated a maximum foam height (typically greater than 400 mls). A hot plate magnetic stirrer maintained process temperature and a homogeneous solution prior to sampling. Aside from the product of Example 1, above, ("Ex. 1") and the antifoam designated HVPDS, a commercial polyalkylglycol antifoam, referred to herein as PAG, and another commercial silicone antifoam referred herein to as SIL, were tested. The results are shown in the following tables:

| Anti-foam | Dose (ppm) | Foam Height (mls) at | | | | | |
|---|---|---|---|---|---|---|---|
| | | 0.5 min. | 1 min. | 2 min. | 3 min. | 4 min. | 5 min. |
| BROTH A | | | | | | | |
| None | — | >400 | | | | | |
| SIL | 100 | 65 | 50 | 45 | 55 | 65 | 90 |
| HVPDS | 100 | 10 | 10 | 10 | 40 | 65 | 75 |
| PAG | 100 | 35 | 30 | 30 | 35 | 40 | 65 |
| Ex. 1 | 100 | 35 | 35 | 35 | 35 | 35 | 35 |
| BROTH B | | | | | | | |
| None | — | 125 | 115 | 115 | 120 | 130 | 155 |
| SIL | 100 | 40 | 45 | 60 | 80 | 110 | 115 |
| HVPDS | 100 | 45 | 45 | 70 | 85 | 115 | 140 |
| PAG | 100 | 60 | 65 | 70 | 85 | 85 | 90 |
| Ex. 1 | 100 | 5 | 5 | 5 | 5 | 5 | 10 |
| Ex. 1 | 100 | 0 | 0 | 10 | 10 | 10 | 10 |
| BROTH C | | | | | | | |
| None | — | 185 | 155 | 160 | 160 | 165 | 175 |
| Ex. 1 | 100 | 0 | 0 | 0 | 10 | 20 | 20 |
| BROTH D | | | | | | | |
| None | — | 110 | 125 | 130 | 140 | 145 | 155 |
| Ex. 1 | 100 | 5 | 10 | 10 | 10 | 5 | 5 |

In view of the above, it will be seen that the several advantages of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A method for controlling foam in a fermentation broth comprising adding to the fermentation broth an effective amount of a composition comprising a compound corresponding to the formula:

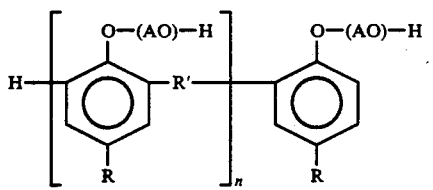

wherein AO is an oxyalkylene copolymer moiety of oxypropylene and oxyethylene units, each oxyalkylene copolymer moiety having a molecular weight of about 300 or more and an oxypropylene to oxyethylene molar ratio of from about 2:1 to about 10:1, n is an integer from about 1 to about 20, R is an alkyl group of from about three to about twelve carbon atoms, and R' is selected from the group consisting of methylene and substituted methylene.

2. A method as set forth in claim 1 wherein the oxyalkylene copolymer moiety has an average molecular weight of about 600 or more.

3. A method as set forth in claim 2 wherein n is an integer from about 1 to about 15.

4. A method as set forth in claim 3 wherein n is an integer from about 6 to about 15.

5. A method as set forth in claim 4 wherein n is about 6 to about 8.

6. A method as set forth in claim 1 wherein the oxyalkylene copolymer moiety has a molecular weight of about 1,200 or more.

7. A method as set forth in claim 6 wherein the oxyalkylene copolymer moiety has a molecular weight of from about 1,200 to about 5,000.

8. A method as set forth in claim 7 wherein the oxyalkylene copolymer moiety has a molecular weight of from about 1,200 to about 3,000.

9. A method as set forth in claim 5 wherein the oxyalkylene copolymer has a molecular weight of about 1,200 or more.

10. A method as set forth in claim 9 wherein the oxyalkylene copolymer has a molecular weight of from about 1,200 to about 5,000.

11. A method as set forth in claim 2 wherein the compound corresponds to the formula:

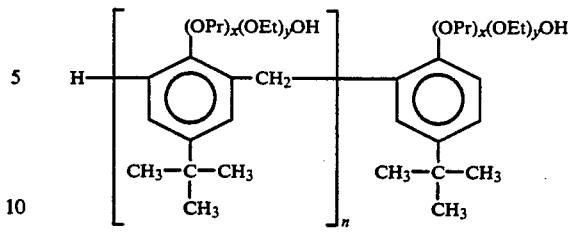

wherein Pr represents propylene, Et represents ethylene, n is an integer from about 1 to about 20, x is an integer from about 20 to about 40 and y is an integer from about 2 to about 10.

12. A method as set forth in claim 11 wherein n is an integer from about 6 to about 14.

13. A method as set forth in claim 12 wherein n is about 6 to about 8.

14. A method as set forth in claim 13 wherein x is about 30.

15. A method as set forth in claim 14 wherein y is about 5.

16. A method as set forth in claim 11 wherein about 50 parts by weight to about 5,000 parts by weight of the compound is added per 1,000,000 parts by weight of the fermentation broth.

17. A method for inhibiting or reducing foam in a fermentation broth comprising adding to a fermentation broth an effective amount of a composition produced by reacting an alkylphenol wherein the alkyl group has from about three to about twelve carbon atoms, with a lower aldehyde in a condensation reaction to produce a condensation product containing a plurality of phenolic units and polyoxyalkylating the condensation product to produce a polyaryalkylated product by subjecting the condensation product to dehydration conditions in the presence of about five or more moles of propylene oxide and about one or more moles of ethylene oxide per mole of phenolic units, the molar ratio of propylene oxide to ethylene oxide being from about 2:1 to about 10:1.

18. A method as set in claim 17 wherein the polyoxyalkylated product is further treated by removing solvent from the polyoxyalkylated product.

19. A method as set forth in claim 18 wherein the polyoxyalkylation step is carried out by reacting the condensation product with from about ten to about 100 moles of propylene oxide and from about two to about thirty moles of ethylene oxide under dehydration conditions.

* * * * *